United States Patent [19]

Sato et al.

[11] 4,127,647

[45] Nov. 28, 1978

[54] PROCESS FOR PREPARATION OF STABLE AMORPHOUS MACROLIDE ANTIBIOTIC SOLIDS

[75] Inventors: Toyomi Sato, Tokyo; Toshiyuki Kobayashi, Yokohama; Takeshi Mayama, Chigasaki; Akira Okada, Zushi, all of Japan

[73] Assignee: Meiji Seika Kaisha, Ltd., Chuo, Japan

[21] Appl. No.: 842,197

[22] Filed: Oct. 14, 1977

Related U.S. Application Data

[63] Continuation-in-part of Ser. No. 674,204, Apr. 5, 1976, abandoned.

[30] Foreign Application Priority Data

Apr. 8, 1975 [JP] Japan .................................. 50-41822

[51] Int. Cl.$^2$ ...................... A61K 31/74; A61K 35/00
[52] U.S. Cl. ........................................ 424/78; 424/35; 424/115; 424/181; 424/362
[58] Field of Search ................... 424/35, 362, 78, 115, 424/181

[56] References Cited

U.S. PATENT DOCUMENTS 3,962,419  6/1976  Mayama et al. ...................... 424/35

Primary Examiner—Sam Rosen
Attorney, Agent, or Firm—Sughrue, Rothwell, Mion, Zinn and Macpeak

[57] ABSTRACT

Amorphous solids of macrolide antibiotics which are stable with the passage of time are prepared by dissolving a macrolide antibiotic and a cellulose polymer selected from the group consisting of ethyl cellulose, hydroxypropyl cellulose and hydroxypropylmethyl cellulose as a stabilizing substance in a volatile organic solvent selected from the group consisting of dichloromethane, 1,1,1-trichloroethane and chloroform and spray drying the resulting solution.

9 Claims, 19 Drawing Figures

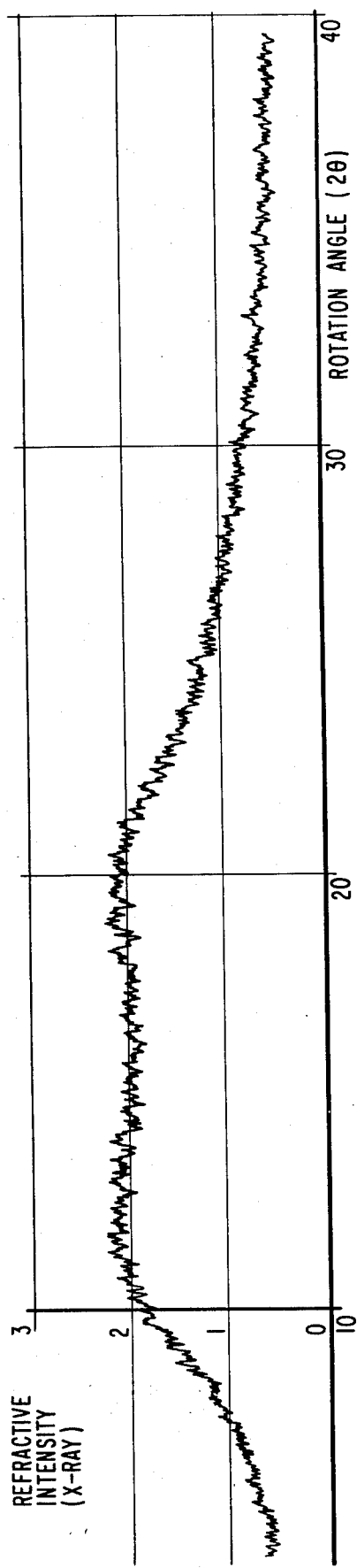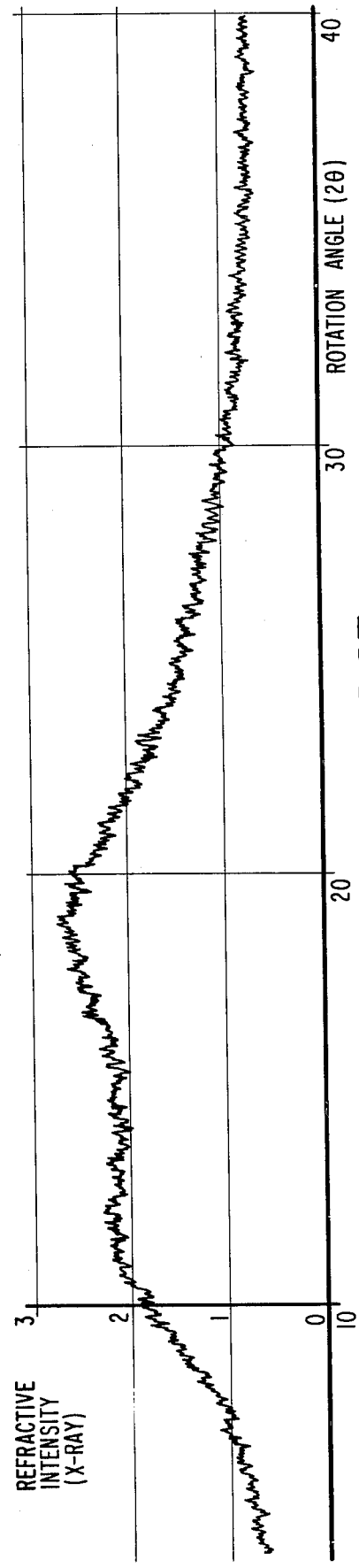

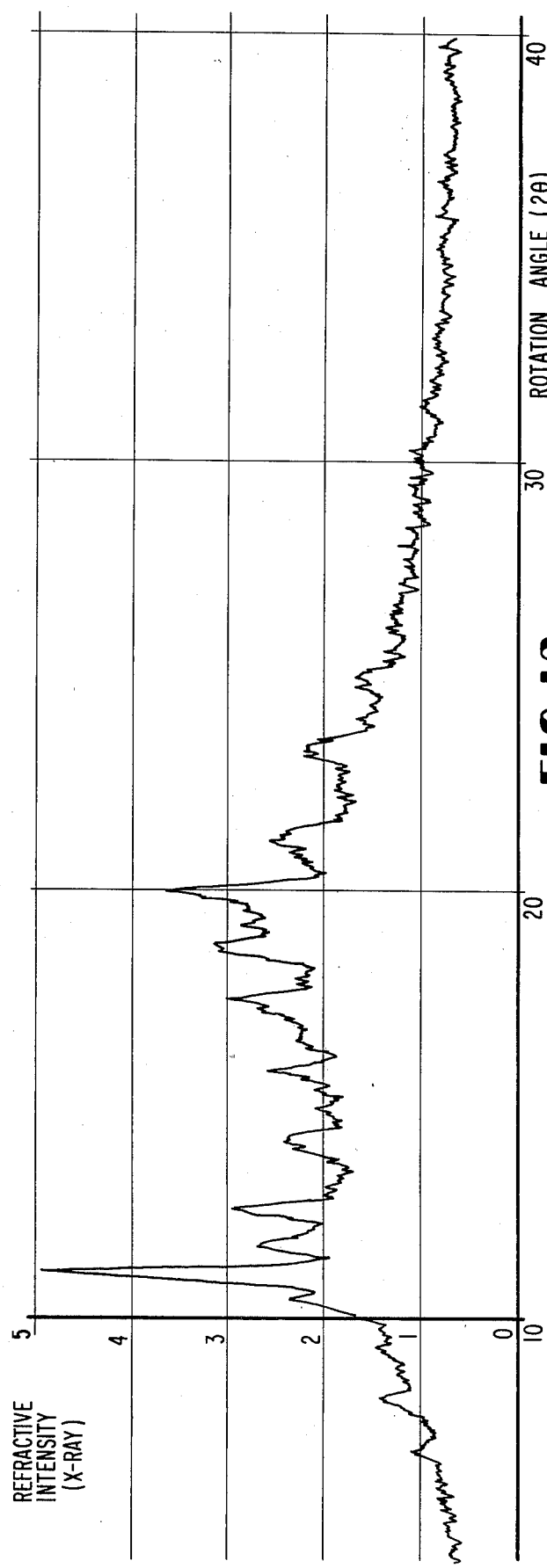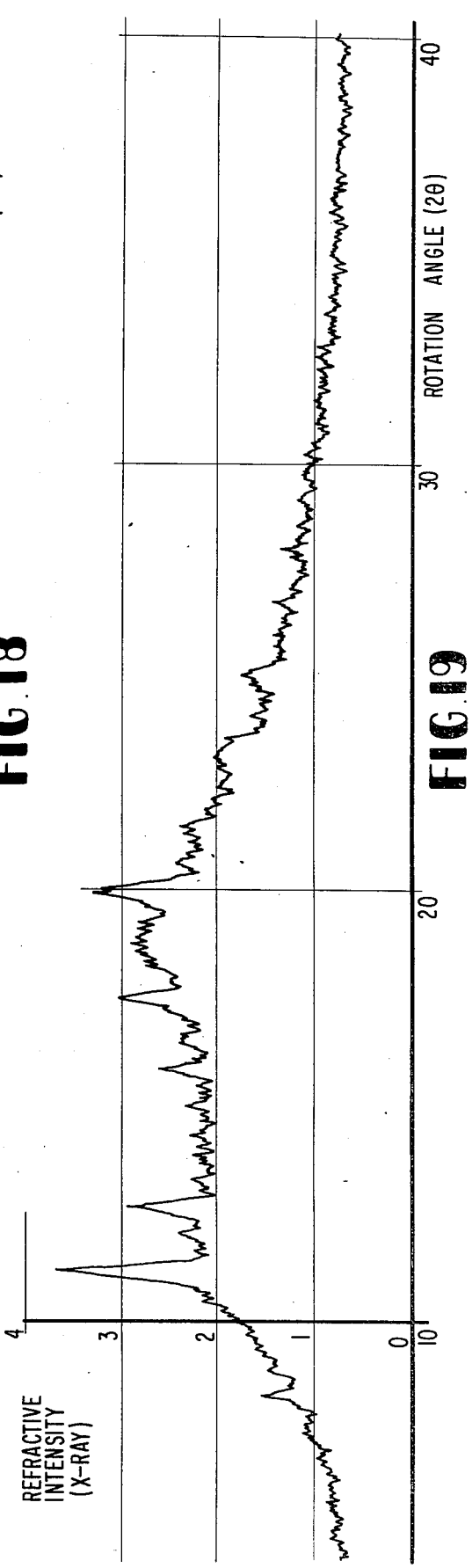

PROCESS FOR PREPARATION OF STABLE AMORPHOUS MACROLIDE ANTIBIOTIC SOLIDS

CROSS REFERENCE TO RELATED APPLICATIONS

This application is a continuation-in-part application of copending U.S. patent application Ser. No. 674,204, filed Apr. 5, 1976, now abandoned.

BACKGROUND OF THE INVENTION

1. Field of the Invention

This invention relates to a process for preparing amorphous solid macrolide antibiotics which are stable with the passage of a long period of time.

2. Description of the Prior Art

A substance which is sparingly soluble in water generally has the property that crystals thereof differ in solubility from the amorphous solid form thereof, and the latter has a higher solubility. This difference in solubility is of great significance in pharmaceutical formulations. For example, macrolide antibiotics (e.g., midecamycin, kitasamycin, josamycin, erythromycin, spiramycin, or derivatives thereof) are sparingly water soluble substances, and in orally administrable formulations such as tablets, capsules or dry syrups of these substances, the use of the amorphous solid form thereof having better solubility, can lead to full effectiveness of these antibiotics.

Since, however, amorphous solids are inherently at a high energy level, they are unstable and apt to change into the crystal form with the passage of time. For example, the Japanese language publication "Method of Designing Pharmaceutical Formulations (2), First Part" (*Lectures in Fundamentals of Development of Pharmaceuticals*, Vol. IX, edited by Masashi Nogami and Kyosuke Tsuda, published by Chijin Shokan) states:

"Amorphous solids frequently assume this state by lyophilization, rapid cooling of a molten liquid, or the co-presence of impurities (a kind of plasticization), but are apt to be converted to a stable crystalline state."

Attempts to obtain amorphous solids of macrolide antibiotics (e.g., midecamycin, 9-acetyl-3"-acetyl-midecamycin, kitasamycin, erythromycin, or josamycin) by ordinary techniques (e.g., lyophilization or the rapid cooling of a molten liquid) result in products containing crystals, or products which are readily converted to crystals with the passage of time, and it is difficult to obtain crystal-free amorphous solids which are stable with the passage of time.

Conventional techniques for the spray drying of macrolide antibiotics are disclosed, for example, in Japanese patent Applications (OPI) Nos. 81526/74, 133513/74 and 132216/74.

Japanese patent application (OPI) No. 81526/74 discloses a process for preparing a coated antibiotic for oral administration free from a bitter taste and a reduction in its effective concentration in blood which comprises dissolving a macrolide antibiotic in a solution or dispersion in an inert volatile organic solvent of a wall forming polymer selected from the group consisting of polyvinyl acetal diethylaminoacetate, cellulose acetate dibutylaminohydroxypropyl ether, a dimethylaminoethyl methacrylate/methacrylate copolymer and ethyl cellulose and at least one material selected from the group consisting of waxes, higher fatty acids and insoluble salts of higher fatty acids, and spray drying the resulting solution.

Japanese patent application (OPI) No. 133513/74, on the other hand, discloses a process for preparing a coated antibiotic for oral administration free from a bitter taste and a reduction in its effective concentration in blood which has a fine particle size and excellent water repellency, which comprises dissolving the macrolide antibiotic in a solution or dispersion in the above organic solvent of the wall forming polymer and at least one material selected from higher fatty acids, waxes, and insoluble salts of higher fatty acids and also a non-toxic mineral oil, vegetable oil, animal oil, surfactant or defoamer soluble in the above organic solvent and having an H.L.B. of not more than about 5, and spray drying the resulting solution.

Furthermore, Japanese patent application (OPI) No. 132216/74 discloses a process for producing a coated macrolide antibiotic suitable for oral administration which has a good shape and is free from bitterness and a reduction in its concentration in blood, the process comprising dissolving a macrolide antibiotic in a solution or dispersion in an inert volatile organic solvent of a wall forming material selected from the group consisting of a styrene/maleic acid copolymer, higher fatty acids, higher fatty acid derivatives and water insoluble salts of higher fatty acids, and spray drying the resulting solution.

The invention of Japanese patent application (OPI) No. 81526/74 requires at least one coating substance selected from the group of wall forming polymers and the group of waxes, higher fatty acids and insoluble salts of higher fatty acids.

In the invention of Japanese patent application (OPI) No. 133513/74, a non-toxic mineral oil, vegetable oil, animal oil, surfactant or defoamer having an H.L.B. of not more than about 5 is further used as a coating material in addition to the coating material used in the invention of Japanese patent application No. (OPI) 81526/74.

The invention of Japanese patent application (OPI) No. 132216/74 is the same as that of Japanese patent application (OPI) No. 81526/74 except that a styrene/maleic acid copolymer is used as the wall forming polymer. The amount of such coating substances is equal to, or larger than, that of the macrolide antibiotic, and they are regarded as effective for the prevention of the bitterness of the antibiotic.

SUMMARY OF THE INVENTION

Our extensive investigations in an attempt to provide a process for producing amorphous solids free from crystals and having good stability with the passage of time led to the discovery that amorphous solids of macrolide antibiotics which are free from crystals and have good stability with the passage of time can be obtained by spray drying a solution in a volatile organic solvent of a macrolide antibiotic and at least one cellulose polymer.

Accordingly, this invention provides a process for preparing amorphous solids of macrolide antibiotics which are stable with the passage of time, the process comprising spray drying a solution in a volatile organic solvent selected from the group consisting of dichloromethane, 1,1,1-trichloroethane and chloroform of a macrolide antibiotic and at least one cellulose polymer selected from the group consisting of ethyl cellulose, hydroxypropyl cellulose and hydroxypropylmethyl cellulose.

BRIEF DESCRIPTION OF THE DRAWINGS

FIGS. 9 to 14 are X-ray diffraction patterns of amorphous solids of macrolide antibiotics produced using stabilizing substances of the present invention produced, respectively, in Examples 1 to 6 after storage for 3 months or longer at 60° C.

FIGS. 15 to 19 are X-ray diffraction patterns of macrolide antibiotics produced in accordance with U.S. Pat. No. 3,962,419 as described in Reference Example 2.

DETAILED DESCRIPTION OF THE INVENTION

Figure 1:
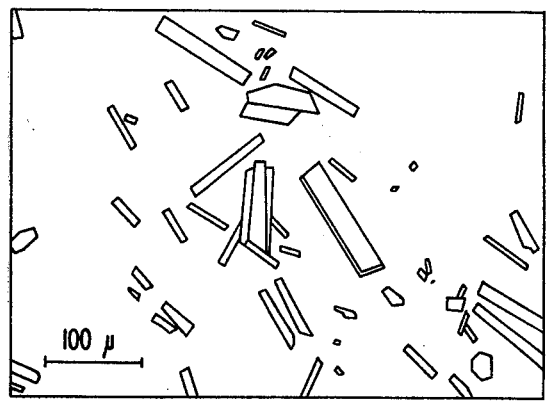
FIG. 1 is a microphotograph of crystals of 9-acetyl-3''-acetylmidecamycin (10 × 10).
Figure 2:
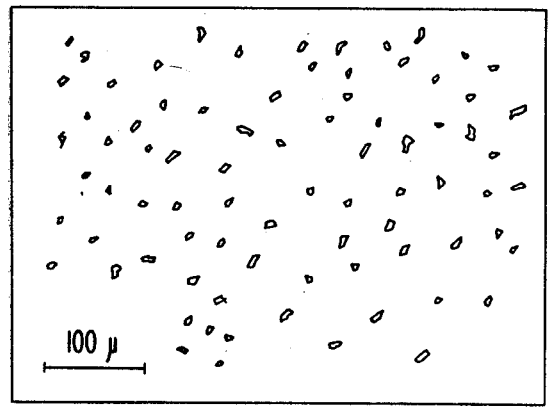
FIG. 2 is a microphotograph of an amorphous solid (10 × 10) of 9-acetyl-3''-acetylmidecamycin obtained by the process of this invention using ethyl cellulose as a stabilizing substance.
Figure 3:
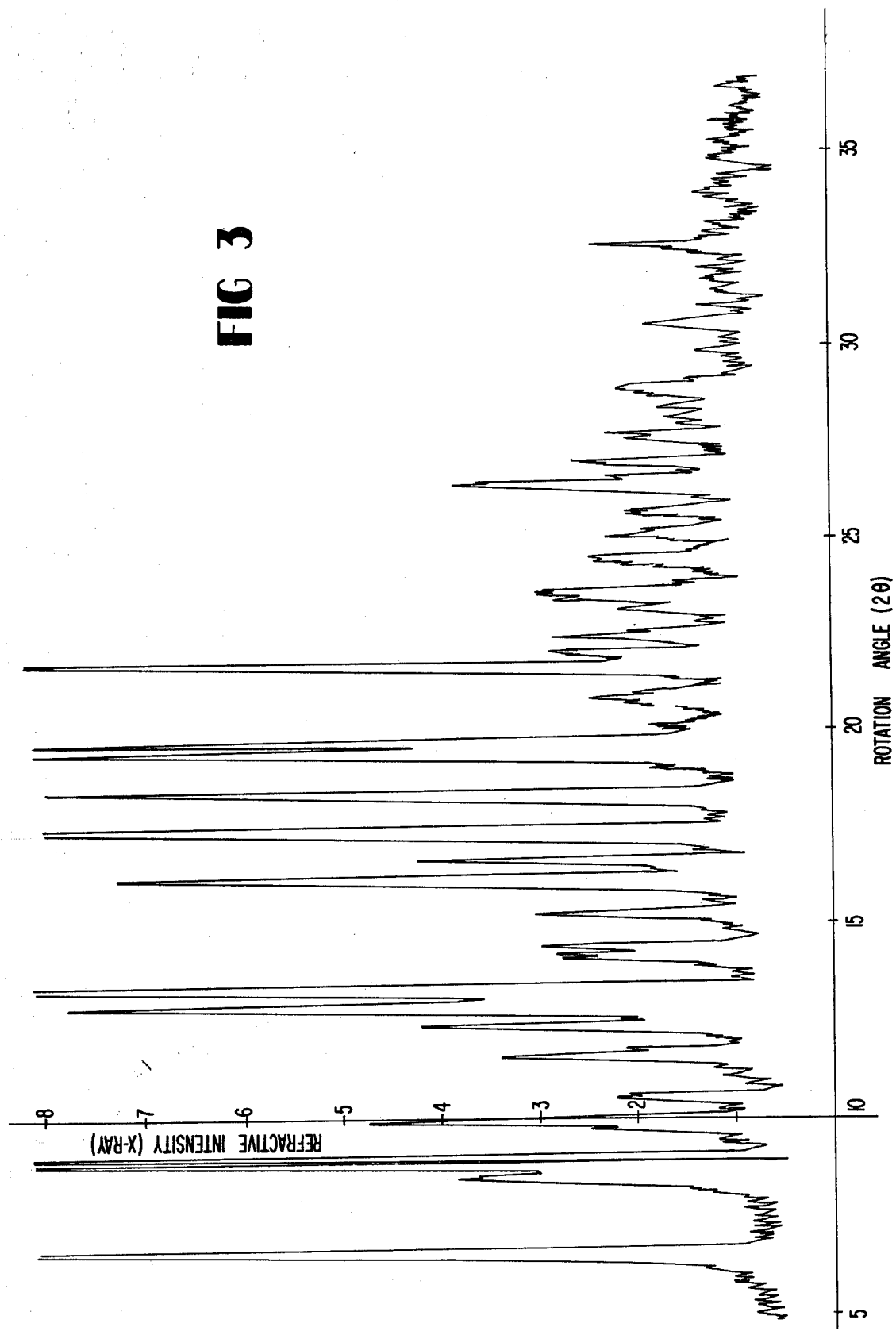
FIG. 3 is an X-ray diffraction pattern of the crystals of 9-acetyl-3''-acetylmidecamycin.
Figure 4:
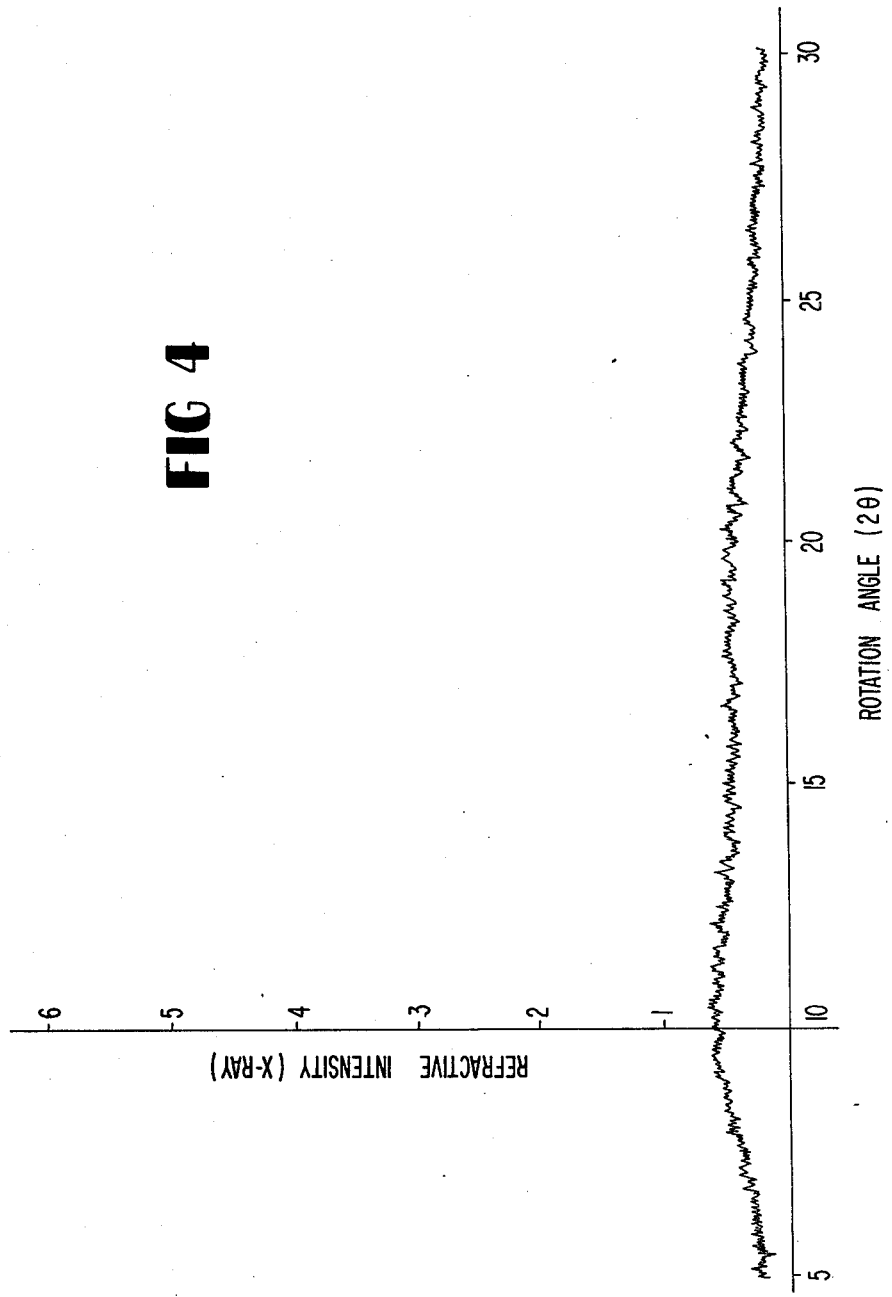
FIG. 4 is an X-ray diffraction pattern of the amorphous solid of 9-acetyl-3''-acetylmidecamycin immediately after preparation by the process of this invention using ethyl cellulose as a stabilizing substance.
Figure 5:
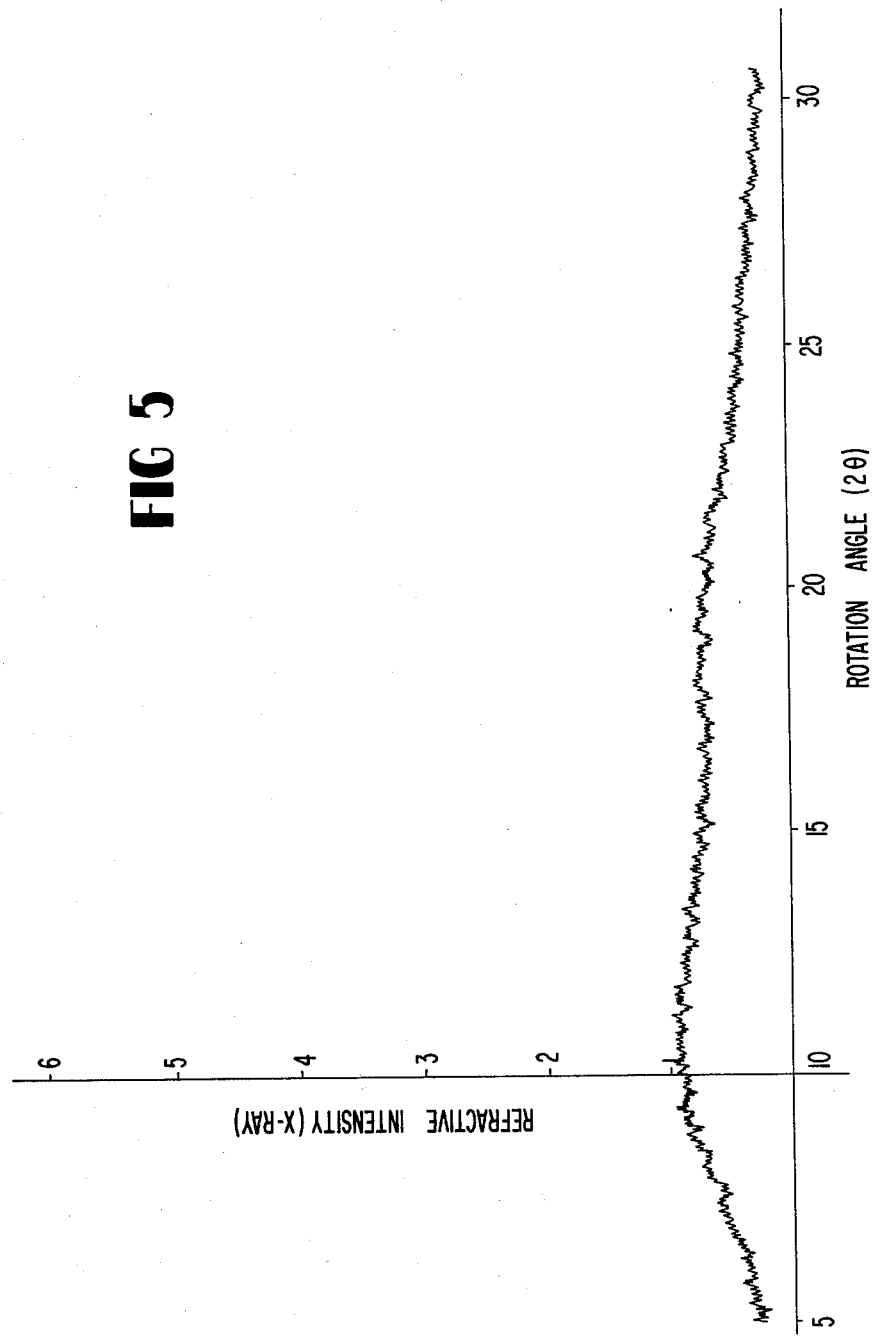
FIG. 5 is an X-ray diffraction pattern of the amorphous solid shown in FIG. 4 after storage for 5 weeks at 60° C.
Figure 6:
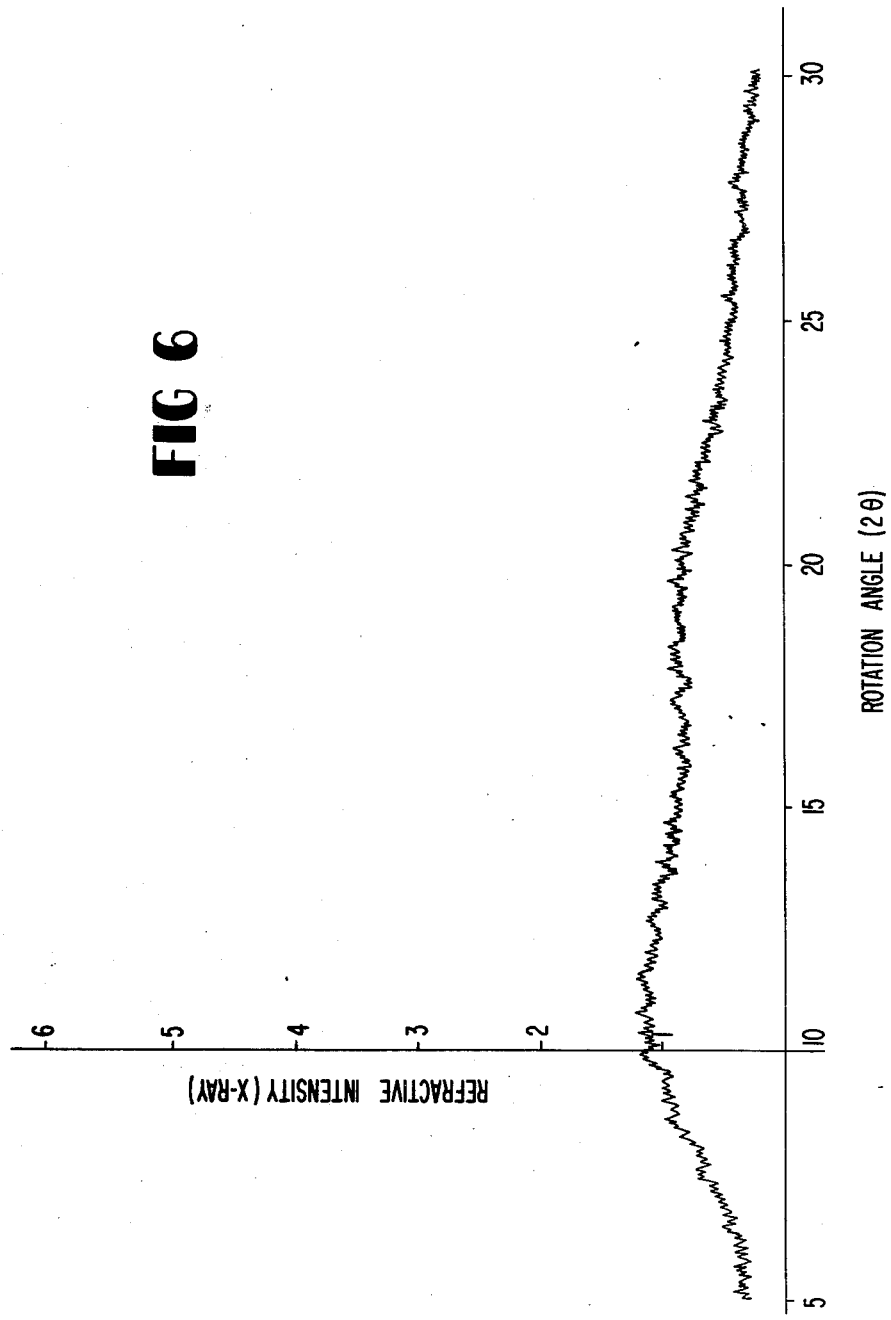
FIG. 6 is an X-ray diffraction pattern of an amorphous solid of 9-acetyl-3'' -acetylmidecamycin immediately after preparation without using the stabilizing substance of the present invention.
Figure 7:
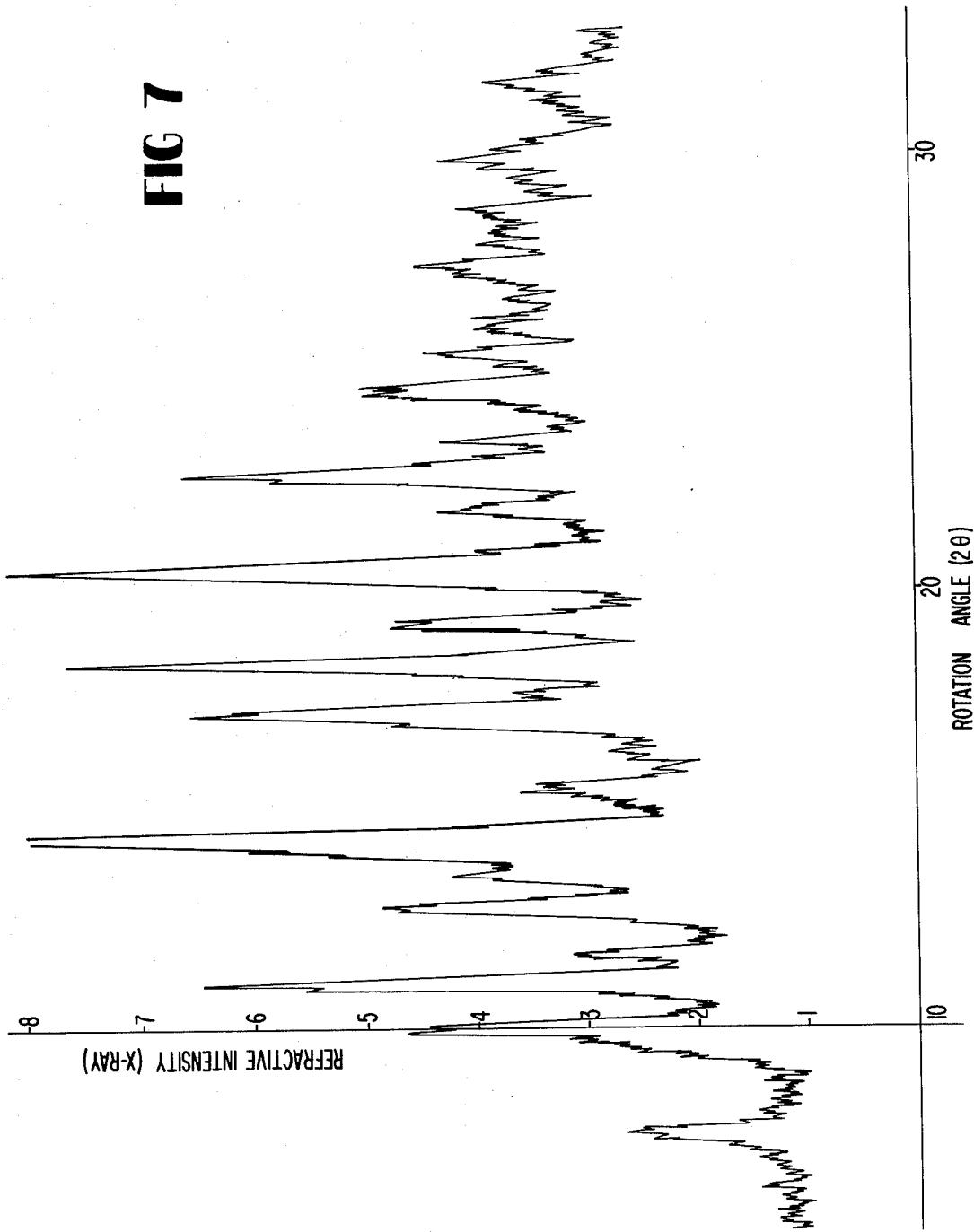
FIG. 7 is an X-ray diffraction pattern of the amorphous solid shown in FIG. 6 after storage for 5 weeks at 60° C.

The present invention provides a process for preparing amorphous solids of macrolide antibiotics having good stability with the passage of time, that is, the capability not to convert to the crystalline form with the passage of time, which comprises spray drying a solution in a volatile organic solvent of a macrolide antibiotic and at least one cellulose polymer.

The process of the present invention is basically different from the three patent publications cited above in that it does not require the waxes, higher fatty acids, insoluble salts of higher fatty acids, mineral oil, vegetable oil, animal oil, surfactant, or defoamer required therein.

For example, an amorphous solid obtained by spray drying a solution of 10 g of 9-acetyl-3''-acetylmidecamycin and 1.5 g of ethyl cellulose in 200 ml of dichloromethane in accordance with the process of this invention does not contain any crystals, and maintains its state even after storage at 60° C. for 7 months. In contrast, a product obtained by spray drying a solution of only the antibiotic in the solvent contains a small amount of crystals even immediately after preparation, and is almost entirely crystallized upon storage at 60° C. for 2 weeks. The presence of crystals was evaluated by the presence or absence of polarized light through a microscope and by X-ray diffraction. The results of the above analysis are shown in FIGS. 1 to 19 of the accompanying drawings.

Using an experimental animal (a rabbit with a body weight of 3.3 to 3.6 kg), the concentration in the blood of the rabbit of amorphous solid 9-acetyl-3''-acetylmidecamycin obtained by the process of this invention using ethyl cellulose as a stabilizing substance was measured in comparison with that of crystalline 9-acetyl-3''-acetylmidecamycin. The results are shown in Table 1 below.

These results demonstrate that the concentration in the blood of the amorphous solid (which is stable with the passage of time and is obtained by the process of this invention) at its maximum shows about twice as large a value as that of the crystalline 9-acetyl-3''-acetylmidecamycin, indicating very good absorption.

Table 1

200 mg (potency)/kg Oral administration
Assay: Sarcina lutea ATCC 9341
Cylinder-plate method Crystalline 9-acetyl-3''-acetylmidecamycin

| Rabbit No. | Time (hours) | | | |
|---|---|---|---|---|
| | 0.5 | 1 | 2 | 4 | 8 |
| 1 | 1.6 | 2.8 | 3.2 | 1.5 | 0 |
| 2 | 3.6 | 4.9 | 3.8 | 2.8 | 0 |
| 3 | 3.3 | 4.2 | 6.2 | 2.0 | 0 |
| x | 2.8 | 4.0 | 4.4 | 2.1 | 0 |

Amorphous solid 9-acetyl-3''-acetylmidecamycin using ethyl cellulose as a stabilizing substance

| Rabbit No. | Time (hours) | | | |
|---|---|---|---|---|
| | 0.5 | 1 | 2 | 4 | 8 |
| 1 | 12.2 | 14.5 | 6.9 | 2.5 | 0 |
| 2 | 4.0 | 6.6 | 4.8 | 2.0 | 0 |
| 3 | 5.8 | 6.6 | 8.4 | 2.4 | 0 |
| x | 7.3 | 9.2 | 6.7 | 2.3 | 0 |

Units of the values: μg (potency)/ml

The cellulose polymer used as a stabilizing substance in this invention is selected from the group consisting of ethyl cellulose, hydroxypropyl cellulose and hydroxypropyl methyl cellulose. The amount of the cellulose polymer added is not limited in particular, and it is usually about 5 to about 40%, preferably about 10 to about 30% (by weight), based on the macrolide antibiotic. The molecular weight of the cellulose polymers is preferably in a range of above about 1,000.

The volatile organic solvent used in this invention is a volatile organic solvent which dissolves the above mentioned polymer and the macrolide antibiotics, volatilizes during spray drying and is selected from the group consisting of chloroform, dichloromethane, and 1,1,1-trichloroethane. Dichloromethane and 1,1,1-trichloroethane are especially preferred.

As is well known, a macrolide antibiotic is an antibiotic which contains a macrocyclic lactone ring and an amino sugar and a carbonyl group bonded thereto through a glycoside linkage as a basic structure. Thus, all antibiotics which are embraced within the above concept and are soluble in the volatile organic solvents described can be used in the present invention. Examples of the macrolide antibiotics are midecamycin, kitasamycin, josamycin, erythromycin, malidomycin, spiramycin, and derivatives of these macrolide antibiotics.

The concentration of the macrolide antibiotic in the volatile organic solvent is not limited in particular. Usually, suitable concentrations are about 5 to about 50%, preferably about 10 to 30%.

The spray drying in accordance with this invention can be carried out using conventional spray driers (e.g., of the nozzle type, disc type, or jet type) with procedures inherent to the use of these devices.

It should be noted, in this regard, that the dosage rate, etc., of the active ingredients of the compositions of the present invention is identical to those for conventional macrolide antibiotics.

Spray drying of a solution in the volatile organic solvent described above of the macrolide antibiotic and the cellulose polymer as described above as a stabilizing substance provides an amorphous solid of the antibiotic which is free from crystals and is stable with the passage of a long period of time.

As one skilled in the art will appreciate, the pressure of spray drying is in accordance with conventional spray drying techniques as such are practiced in the art. Generally, the pressure of spray drying is determined by the type of spray drier employed and the temperature is above about 60° C. but, of course, below any temperature which would degrade or decompose any of the materials being sprayed dried. The time of spray drying, of course, is quite short, and in accordance with times as are conventionally used in the art for spray drying materials.

The following Reference Examples and Examples illustrate the present invention in greater detail.

The pressure employed for spray drying was atmospheric throughout.

Evaluation of the crystals in the following Reference Examples and Examples was determined by the presence or absence of polarized light through a microscope and by X-ray diffraction.

REFERENCE EXAMPLE 1

10 g of 9-acetyl-3''-acetylmidecamycin was dissolved in 200 ml of a chloroform solution containing 4 g of hydroxypropylmethyl cellulose phthalate (mean molecular weight: about 1,000) as a stabilizing substance. The resulting solution was dried at 100° C. and at atmospheric pressure using a spray drier of the disc type for about 10 minutes. An amorphous solid was initially obtained.

Figure 8:
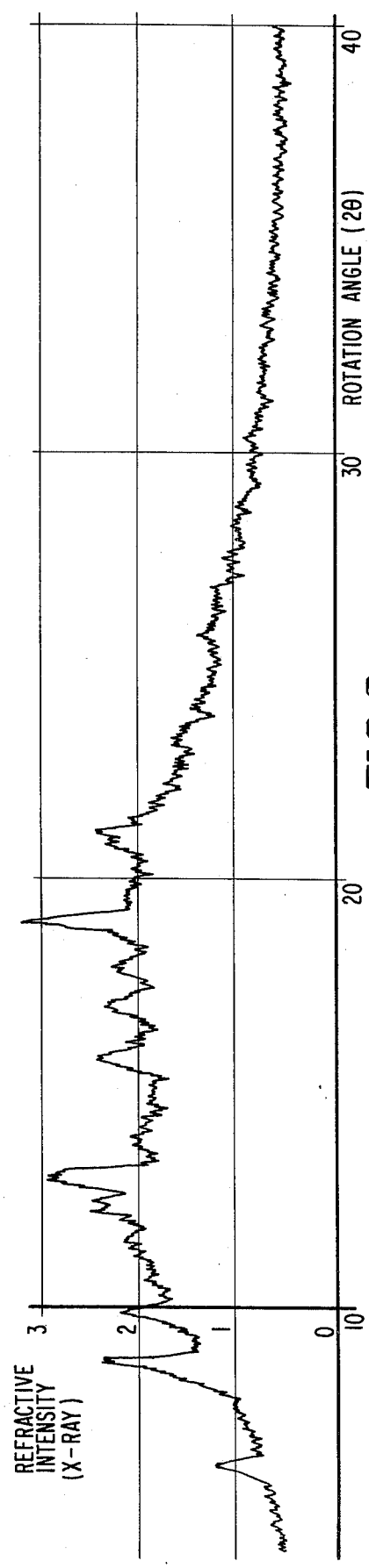
FIG. 8 is an X-ray diffraction pattern of an amorphous solid of 9-acetyl-3''-acetylmidecamycin produced using a stabilizing substance outside the scope of the present invention as described in Reference Example 1 after storage for 3 months at 60° C.

When this product was stored at 60° C. for 6 weeks, it remained as an amorphous solid but after storage at 60° C. for 3 months the amorphous solid became crystalline as shown in FIG. 8.

An amorphous solid of the same antibiotic prepared by spray drying in the above manner except that the stabilizing substance was not used became almost entirely crystalline after storage at 60° C. for 2 weeks.

EXAMPLE 1

Figure 9:
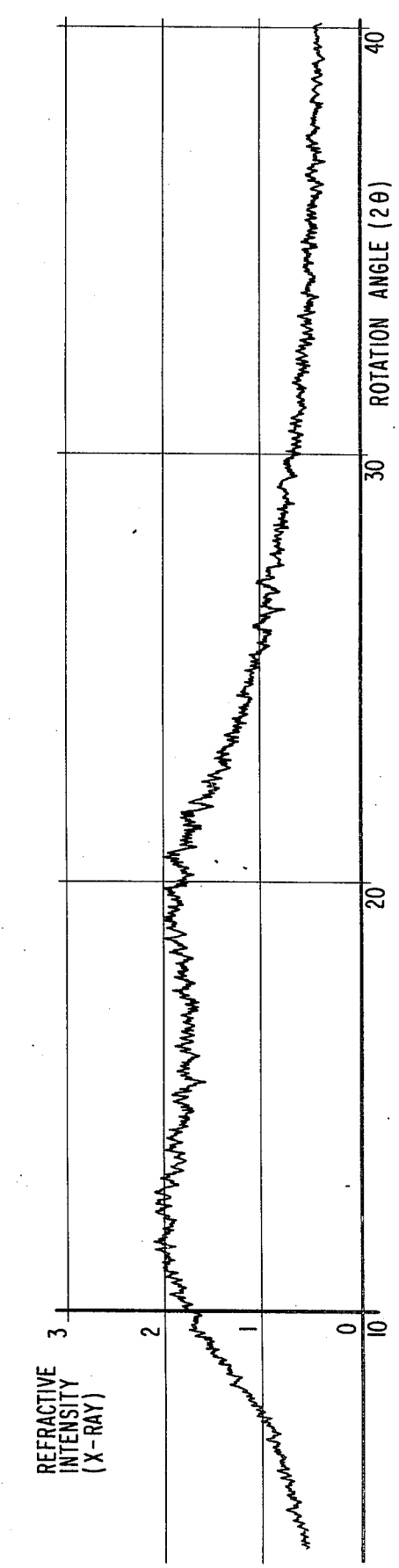

10 g of 9-acetyl-3''-acetylmidecamycin and 1 g of hydroxypropylmethyl cellulose (mean molecular weight: about 1,000) and 1 g of ethyl cellulose (mean molecular weight: about 1,000) as a stabilizing substance were dissolved in 250 ml of 1,1,1-trichloroethane. The resulting solution was spray dried at about 130° C. for about 10 minutes using a spray drier of the jet type to provide a stable amorphous solid. When this product was stored at 60° C. for 3 months, it still remained as an amorphous solid as shown in FIG. 9.

An amorphous solid obtained in the above manner except that the stabilizing substances were not used became almost entirely crystalline after storage at 60° C. for 1 week.

EXAMPLE 2

Figure 10:
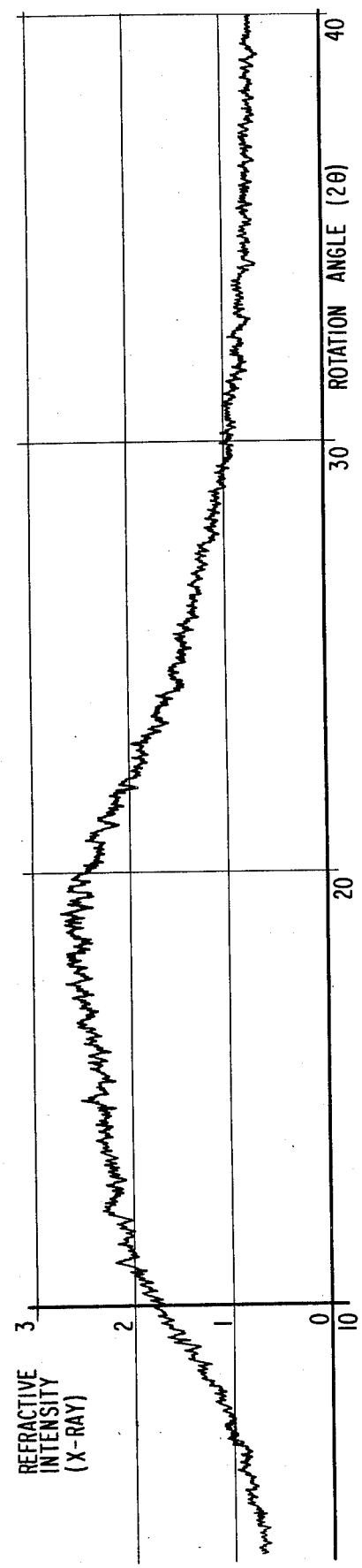

5 g of kitasamycin was dissolved in 150 ml of a chloroform solution containing 0.3 g of hydroxypropyl cellulose (mean molecular weight: about 1,000) as a stabilizing substance. The resulting solution was spray dried at about 100° C. for about 10 minutes using a spray drier of the disc type to provide a stable amorphous solid. When this product was stored at 60° C. for 4 months, it still remained as an amorphous solid as shown in FIG. 10.

An amorphous solid obtained in the above manner except that the stabilizing substance was not used became partly crystalline after storage for 1 month at 60° C.

EXAMPLE 3

Figure 11:
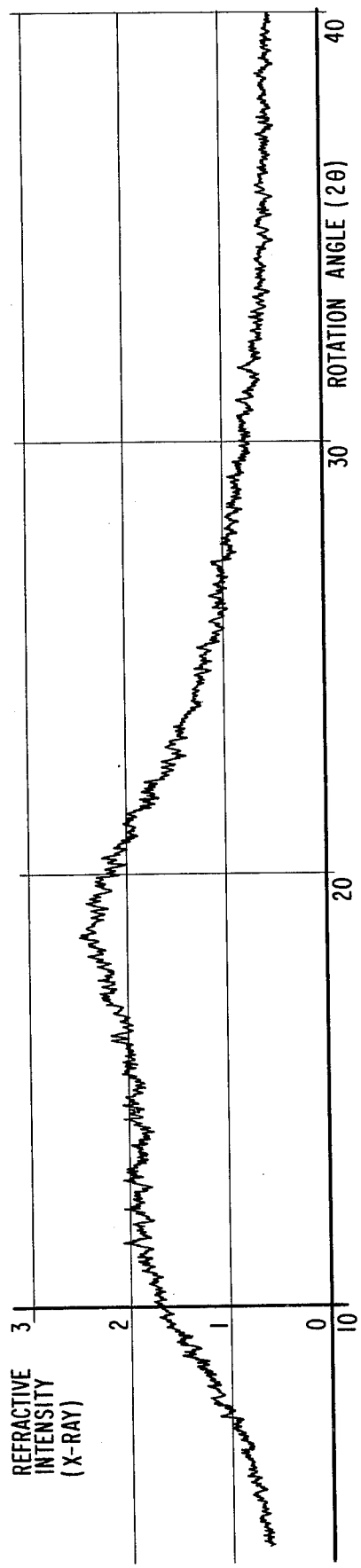

3 g of josamycin was dissolved in 300 ml of chloroform containing 0.1 g of ethyl cellulose (mean molecular weight: about 1,000) and 0.05 g of hydroxypropyl cellulose (mean molecular weight: about 1,000). The resulting solution was spray dried at about 130° C. for about 10 minutes using a spray drier of the jet type to provide a stable amorphous solid. When this product was stored at 60° C. for 3 months, it still remained as an amorphous solid as shown in FIG. 11.

An amorphous solid obtained in the above manner except that the stabilizing substances were not added became partly crystalline after storage at 60° C. for 2 weeks.

EXAMPLE 4

Figure 12:
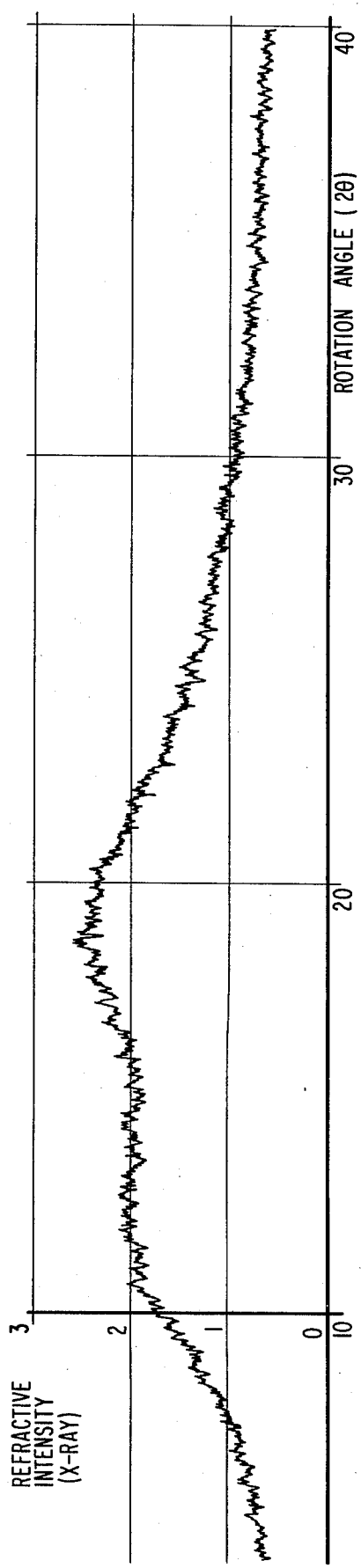

10 g of midecamycin was dissolved in 300 ml of benzene, and 0.5 g of hydroxypropylmethyl cellulose (mean molecular weight: about 1,000) was added to the solution. The resulting solution was spray dried at about 150° C. for about 10 minutes using a spray drier of the jet type to provide a stable amorphous solid. When this product was stored at 60° C. for 3 months, it still remained as an amorphous solid as shown in FIG. 12.

An amorphous solid obtained in the above manner except that the stabilizing substance was not added became partly crystalline after storage at 60° C. for 2 weeks.

EXAMPLE 5

Figure 13:
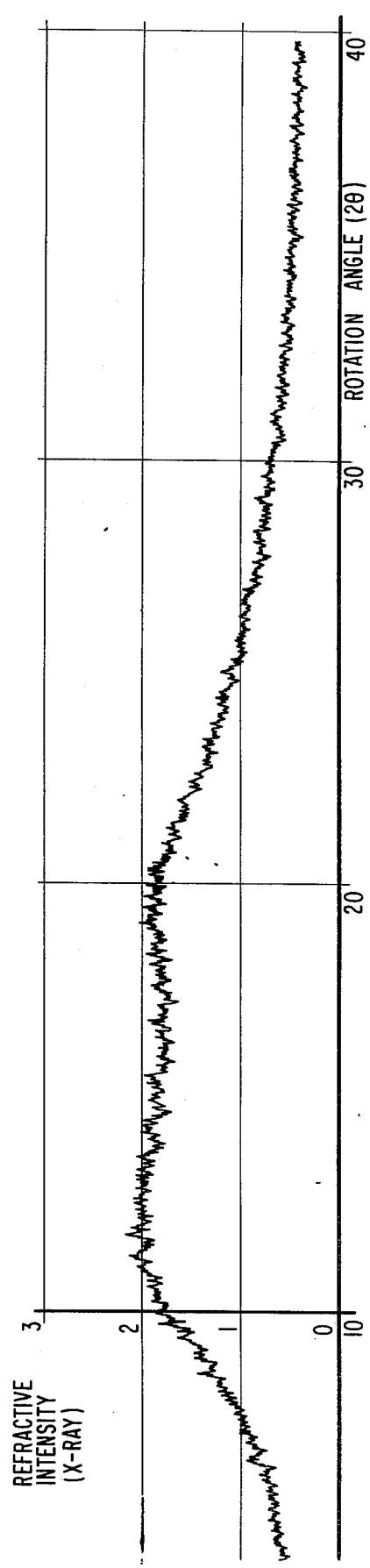

10 g of 9-acetyl-3''-acetylmidecamycin was dissolved in 200 ml of dichloromethane containing 1.5 g of ethyl cellulose (mean molecular weight: about 1,000). The resulting solution was spray dried at about 100° C. for about 10 minutes using a spray drier of the jet type. When this product was stored at 60° C. for 7 months, it still remained as an amorphous solid as shown in FIG. 13.

An amorphous solid obtained in the above manner except that the stabilizing substance was not added became almost entirely crystalline after storage at 60° C. for 2 weeks.

EXAMPLE 6

10 g of 9-acetyl-3''-acetylmidecamycin was dissolved in 100 ml of a chloroform solution containing 2 g of hydroxypropyl cellulose (mean molecular weight: about 1,000) as a stabilizing substance. The resulting solution was spray dried at about 100° C. for about 10 minutes using a spray drier of the disc type to provide a stable amorphous solid. When this product was stored at 60° C. for 4 months, it still remained as an amorphous solid as shown in FIG. 14.

An amorphous solid obtained in the above manner except that the stabilizing substance was not used became almost entirely crystalline after storage for 4 weeks at 60° C.

REFERENCE EXAMPLE 2

U.S. Pat. No. 3,962,419 discloses the stabilization of macrolide antibiotics to acidic environments. The method of stabilization of macrolide antibiotics in the amorphous form as in the present invention is not disclosed in U.S. Pat. No. 3,962,419. In order to demonstrate this, the procedures of the Examples of U.S. Pat. No. 3,962,419 were repeated.

Figure 15:
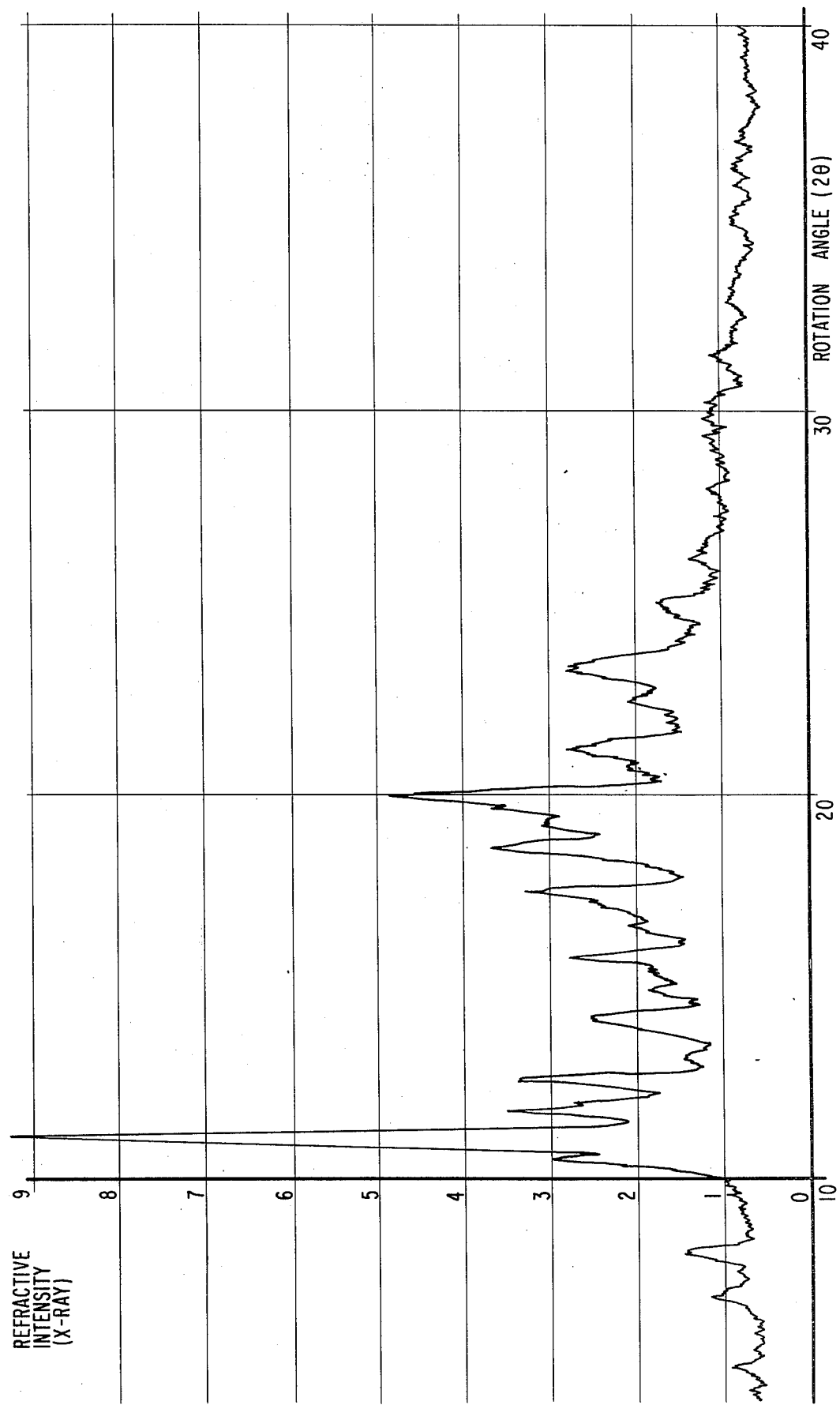
Figure 16:
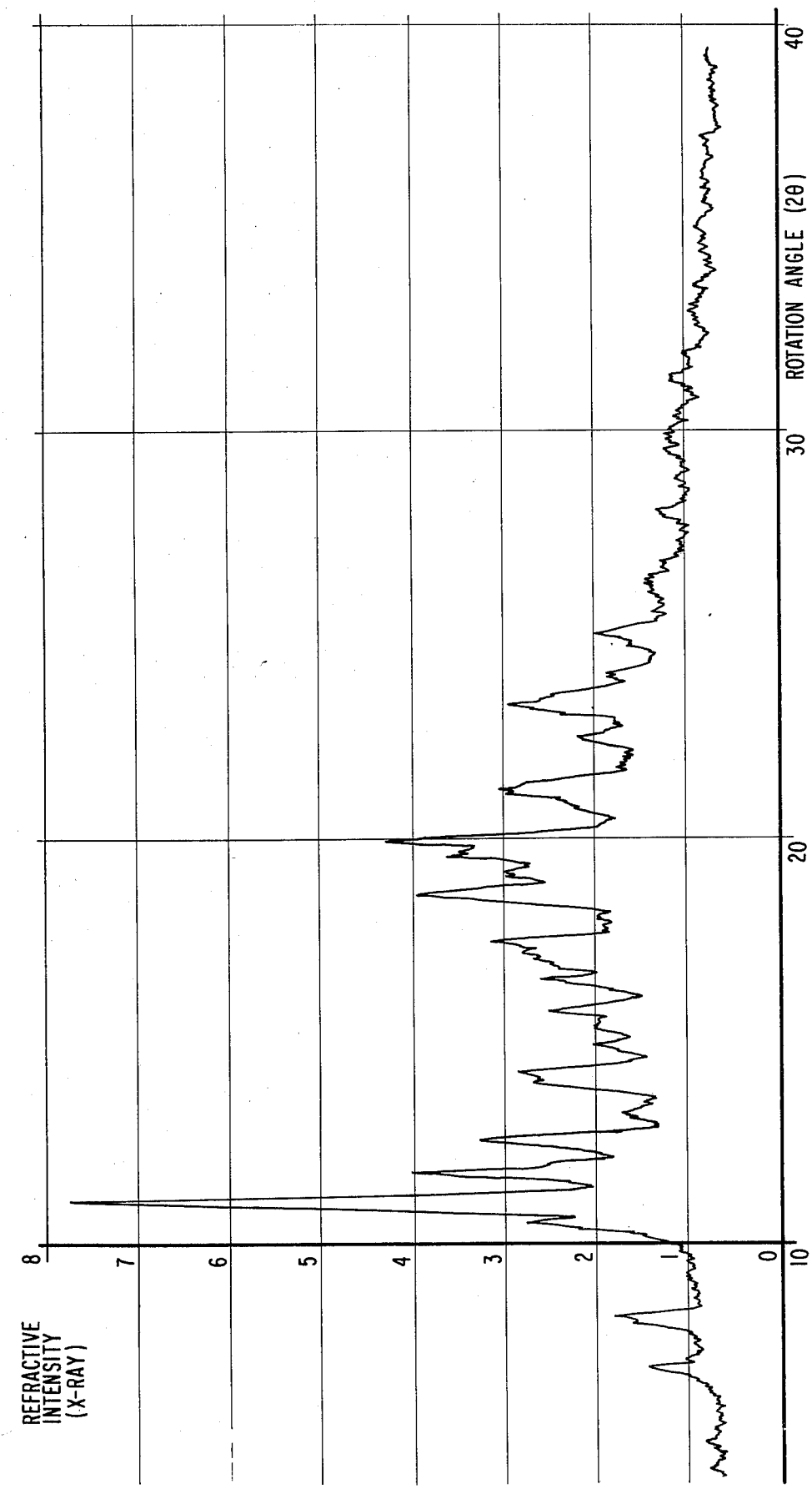

For example, macrolide antibiotics in an amorphous solid form could not be obtained using the procedures of Examples 1 and 3–8 of U.S. Pat. No. 3,962,419. This is demonstrated by FIGS. 15 and 16 which are X-ray diffraction patterns of macrolide antibiotics immediately after preparation using the process of Examples 3 and 6 of U.S. Pat. No. 3,962,419 which are considered representative thereof. FIGS. 15 and 16 clearly show the products of these examples are crystals.

Using the procedures of Example 2 of U.S. Pat. No. 3,962,419, an amorphous solid immediately after the preparation was obtained as shown in FIG. 17. However, this amorphous solid form gradually changed to a crystalline form as shown in FIGS. 18 and 19.

More specifically, FIG. 18 shows the X-ray diffraction pattern of antibiotic SF-837 obtained by Example 2 of U.S. Pat. No. 3,962,419 after storage for 3 months at 41° C. at a humidity of 81% RH.

FIG. 19 shows the X-ray diffraction pattern of antibiotic SF-837 obtained by Example 2 of U.S. Pat. No. 3,962,419 after storage for 3 months at 60° C.

Thus, in contrast to the situation with the present invention, the antibiotic SF-837 obtained by Example 2 of U.S. Pat. No. 3,942,419, although initially an amorphous antibiotic, is an unstable amorphous antibiotic.

While the invention has been described in detail and with reference to specific embodiments thereof, it will be apparent to one skilled in the art that various changes and modifications can be made therein without departing from the spirit and scope thereof.

What is claimed is:

1. A process for preparing amorphous solids of macrolide antibiotics which are stable with the passage of time, said process consisting of spray drying a solution in a volatile organic solvent selected from the group consisting of dichloromethane, 1,1,1-trichloroethane and chloroform of a macrolide antibiotic and at least one cellulose polymer selected from the group consisting of ethyl cellulose, hydroxypropyl cellulose and hydroxypropylmethyl cellulose.

2. The process of claim 1, wherein said solvent is dichloromethane or 1,1,1-trichloroethane.

3. The process of claim 1, wherein the amount of said cellulose polymer is about 5 to about 40% by weight based on the weight of the macrolide antibiotic.

4. The process of claim 3, wherein the amount of said cellulose polymer is about 10% to about 30% by weight based on the weight of the macrolide antibiotic.

5. The process of claim 1, wherein the concentration of the macrolide antibiotic in the volatile organic solvent is about 5 to about 50% by weight.

6. The process of claim 5, wherein the concentration of macrolide antibiotic in the volatile organic solvent is about 10 to about 30% by weight.

7. The process of claim 1, wherein said cellulose polymer has a molecular weight of above about 1,000.

8. The process of claim 1, wherein said spray drying is conducted at a temperature of above about 60° C.

9. A composition comprising at least one amorphous solid macrolide antibiotic and a cellulose polymer prepared by the process of claim 1.

* * * * *